United States Patent [19]

Korsatko et al.

[11] Patent Number: 4,902,516
[45] Date of Patent: Feb. 20, 1990

[54] BINDER-FREE GRANULES WITH DELAYED RELEASE OF THE ACTIVE COMPOUND

[75] Inventors: Werner Korsatko; Brigitta Korsatko-Wabnegg, both of Graz, Austria

[73] Assignee: Chemie Holding Aktiengesellschaft, Linz, Austria

[21] Appl. No.: 178,107

[22] Filed: Apr. 6, 1988

[30] Foreign Application Priority Data

Apr. 10, 1987 [DE] Fed. Rep. of Germany ....... 3712095

[51] Int. Cl.$^4$ ................................................ A61K 9/16
[52] U.S. Cl. ..................................... 424/497; 424/470; 424/482
[58] Field of Search ............... 424/482, 489, 490, 497, 424/470

[56] References Cited

U.S. PATENT DOCUMENTS

| | | | |
|---|---|---|---|
| 3,773,919 | 11/1973 | Boswell et al. | 424/78 |
| 4,166,800 | 9/1979 | Fong | 252/316 |
| 4,384,975 | 5/1983 | Fong | 424/497 X |
| 4,491,575 | 1/1985 | Korsatko | 424/78 X |
| 4,656,024 | 4/1987 | Laruelle | 424/497 X |
| 4,666,702 | 5/1987 | Junginger | 424/497 |
| 4,675,189 | 6/1987 | Kent et al. | 424/497 X |
| 4,728,513 | 3/1988 | Ventouras | 424/46 L |

FOREIGN PATENT DOCUMENTS

| | | |
|---|---|---|
| 0149744 | 11/1984 | European Pat. Off. . |
| 0164571 | 5/1985 | European Pat. Off. . |
| 0172422 | 7/1985 | European Pat. Off. . |
| 6602562 | 7/1968 | Fed. Rep. of Germany . |
| 2620456 | 11/1977 | Fed. Rep. of Germany . |
| 2917037 | 12/1980 | Fed. Rep. of Germany . |

OTHER PUBLICATIONS

Juni et al; "Controlled Release of Aclarubicin . . . " (1986); Chemical Abstracts, vol. 105, p. 401, Ref 85 056g.

Primary Examiner—Thurman K. Page
Attorney, Agent, or Firm—Mark Dryer

[57] ABSTRACT

Binder-free granules for oral and parenteral administration with delayed release of the active compound, consisting of a pharmaceutical active compound or granules thereof and a coating of 1 to 20% by weight of poly-D(—)-3-hydroxybutyric acid, based on the total weight, and a process for their preparation.

10 Claims, No Drawings

BINDER-FREE GRANULES WITH DELAYED RELEASE OF THE ACTIVE COMPOUND

The invention relates to binder-free granules with delayed release of the active compound.

It is known that for certain active compounds it is advantageous to prepare drug forms which release the active compound continuously over a prolonged period of time. Galenical presentation forms with a delayed release of the active compound for oral, parenteral and topical administration have therefore been developed for a number of pharmacologically active substances.

Such a sustained release action can be achieved, for example, by coating powders and granules with acrylic resin lacquers. These coatings and usually also the drug forms to be coated contain additional auxiliaries and fillers, but above all acrylic resin lacquers are exogenous substances and are not biologically degradable.

According to U.S.-PS 3,773,919, certain biologically degradable polymers, in particular polyglycolic acid, polylactic acid and copolymers of lactic and glycolic acid, can be used for the preparation of sustained release forms. These sustained release forms can thereby be prepared (A) by coating, such as spray-drying, fluidized bed coating or microencapsulation, (B) by embedding or (C) by intimate mixing, such as dissolving the active compound and polymer in a solvent and evaporating off the solvent. In the examples, however, only preparation of sustained release forms by "embedding" is described, that is to say the polylactide is melted, the active compound is introduced and suspended in the melt and the melt is allowed to solidify and is ground into small particles. In this method, however, there is the risk that the active compound will be thermally decomposed. On reworking the fluidized bed granulation method described there in the general section under (A), it was found that the polylactides mentioned therein are not suitable for fluidized bed granulation, since the polymer solution was always drawn into threads when sprayed in different concentrations and using different solvents and it was not possible to obtain uniform coating of the active compound.

It is known from U.S.-PS 4,491,575 that poly-D(—)-3-hydroxybutyric acid, called poly-HB below, can be used as a polymeric carrier material, the poly-HB being mixed directly with the active compound and the mixture being pressed to tablets in which the active compound is uniformly distributed in a poly-HB matrix. However, at least 20% by weight of poly-HB is needed to achieve a sustained release action of several hours. This is a disadvantage in particular for medicaments which must be given in high doses and therefore contain large amounts of active compound. Moreover, there are problem medicaments which have adverse osmotic properties, so that a stable matrix can be built up and a good sustained release action achieved only with a poly-HB content of more than 50% by weight. Tablets which contain, for example, 200 mg of active compound must accordingly be mixed with at least 200 mg of poly-HB in this method. The tablets thereby formed weigh more than 400 mg and are so large that they are already unpleasant and even difficult for the patient to take. There was thus the object of preparing sustained release tablets which contain only small amounts of biologically degradable polymeric material and at the same time have a high sustained release action, a large amount of active compound being contained in a relatively small sustained release tablet.

It has now been found that it is possible, starting from an active compound or granules thereof, to prepare, with the aid of poly-HB, binder-free granules which are coated with only a small amount of poly-HB and at the same time have a good sustained release action and can be pressed to tablets without the addition of auxiliaries.

The invention accordingly relates to binder-free granules for oral and parenteral administration with delayed release of the active compound comprising a pharmaceutical active compound or granules thereof and poly-D(—)-3-hydroxybutyric acid having a molecular weight of about 50,000 to about 800,000 wherein the active compound or granules thereof is/are coated with an amount of 1 to 20% by weight of said poly-D(—)-3-hydroxybutyric acid, based on the total weight.

The granules according to the invention consist only of the active compound or granules thereof coated with a certain content of poly-HB. They have good flow properties and, surprisingly, can be pressed to tablets without problems with no additional auxiliaries or fillers.

In principle, any active compound or granules thereof can be used and comprehensive use possibilities are thus achieved. One example of this is the active compound 7-hydroxyethyltheophylline. The invention is of particular importance for tablets with large amounts of active compound, since the size of the tablets can be decreased considerably by the reduced poly-HB content. Examples of such active compounds are celiprolol hydrochloride, hexobendine dihydrochloride, ibuprofen, diclofenac-Na and the like.

The sustained release action achieved depends on the one hand on the physical properties of the active compound used and on the other hand on the thickness of the coating with poly-HB and on the molecular weight of the poly-HB used. The thicker the coating and/or the higher the molecular weight of the poly-HB used, the more slowly the active compound is released, so that for each active compound there are two parameters for achieving a desired period of sustained release. The poly-HB coating is 1 to 20% by weight, based on the total weight of the granules, preferably 1 to 15% by weight. The range from 3 to 10% by weight is particularly preferred.

It is an essential feature of the invention that a large amount of active compound can be coated with a little poly-HB, good sustained release properties nevertheless being achieved.

The degradation product of poly-HB, D(—)-3-hydroxybutyric acid, is an endogenous substance and can therefore have no metabolic disadvantages.

The poly-HB used is prepared, for example, biotechnologically in accordance with EP-A-0,149,744 by aerobic culture of a microorganism of the Alcaligenes genus. A poly-Hb with a molecular weight of about 50,000 to about 800,000 is employed for preparation of the granules according to the invention, the range from 100,000 to 400,000 being particularly preferred.

The invention also relates to a process for the preparation of binder-free granules, which comprises spraying a pharmaceutical active compound or granules thereof with a solution of poly-D(—)-3-hydroxybutyric acid in a granulating process and evaporating off the solvent, the pharmaceutical active compound or granules theref being coated with an amount of 1 to 20% by weight of poly-D(—)-3-hydroxybutyric acid based on the total weight. In this process, poly-HB is dissolved in a suitable solvent, such as, for example, methylene chloride or chloroform. The amount of solvent depends of the nature of the solvent, the molecular weight of the poly-HB used and the spraying temperature. The spraying temperature is, for example, between 35° and 50° C. The active compound is used as a powder or as granules and is then sprayed with a solution of poly-HB by any desired building-up granulation process, after which the granules according to the invention are obtained after evaporating off the solvent.

The use of fluidized bed granulation is particularly advantageous, since all the process steps are carried out in the same vessel in this process. The active compound or granules thereof are initially taken and sprayed with a poly-HB solution. A fluidized bed is built up and maintained by feeding in air or an inert gas, the active compound or granules thereof being coated with a thin layer of poly-HB during evaporation of the solvent.

Porous granules of spherical shape which can be pressed to compressed tablets of any desired form without the addition of binders or other auxiliaries are formed.

EXAMPLE 1

100 g of celiprolol hydrochloride granules were initially taken in a fluidized bed granulation vessel and sprayed with 300 ml of a solution of 6 g of poly-D(−)-3-hydroxybutyric acid in chloroform (2% strength solution) of molecular weight 142,935 under a spraying pressure of 1 bar and at a temperature of 40° C. By blowing in air, a fluidized bed was thereby built up and the solvent was evaporated off, the granules being provided with a thin coating of poly-HB.

The content of poly-HB in the fluidized bed granules (FBG) was 5 to 6%, based on the total weight. Tablets were prepared from the resulting granules under a pressure of 2.5 t, which corresponds to 245.3 N/mm².

| | |
|---|---|
| Bulk volume of the FBG: | 3.8 ml/g |
| Settled volume of the FBG: | 3.09 ml/g |
| Tablet size: | d = 9.2 mm h = 4.2 mm |
| Average weight of the tablets: | 218.8 mg ± 5.3 mg (±2.4%) |
| Breaking strength: | 19.61 kp |

Granules and tablets for Examples 2 to 9 were also prepared in an analogous manner.

TABLE I

| Example | Active compound | Molecular weight of poly-HB | % poly-HB | Solvent | Spraying temperature °C. |
|---|---|---|---|---|---|
| 1 | celiprolol hydrochloride | 142,935 | 5–6 | CHCl₃ | 40 |
| 2 | celiprolol hydrochloride | 142,935 | 4–5 | " | 40 |
| 3 | celiprolol hydrochloride | 278,726 | 2–3 | " | 40 |
| 4 | celiprolol hydrochloride | 278,726 | 3–4 | " | 40 |
| 5 | celiprolol hydrochloride | 604,691 | 1–2 | " | 40 |
| 6 | 7-hydroxy-ethyltheophylline | 604,691 | 1 | CHCl₃ | 40 |
| 7 | hexobendine dihydrochloride | 604,691 | 1 | " | 40 |
| 8 | ibuprofen | 604,691 | 1 | " | 40 |
| 9 | diclofenac-Na | 604,691 | 1 | " | 40 |

In vitro release of the active compound

To measure the sustained release properties of the celiprolol hydrochloride tablets (Examples 1 to 5), the tablets were shaken in 100 ml of 0.9% strength sodium chloride solution at 37° C. in closed brown glass bottles and analyzed for the amount of active compound released at intervals of 30 and 60 minutes. The half-change method, in which the pH is increased continuously from pH 1.3 to pH 7.3 in the course of 8 hours, the release of active compound being measured at intervals as above, was also used for the investigation and gave the same results. Quantitative analytical detection of celiprolol was by spectrophotometry in a suitable dilution as 324 nm. The sustained release properties of the tablets containing the other active compounds (Examples 6 to 9) were determined by the half-change method. Quantitative analytical detection was by spectrophotometry (7-hydroxyethyltheophylline: 273 nm, hexobendine dihydrochloride: 266 nm, ibuprofen: 264 nm, diclofenac-Na: 275 nm).

TABLE II

AMOUNT OF ACTIVE COMPOUND RELEASED in % by weight, based on the total content

| Example | 0,5 | 1 | 2 | 3 | 4 | 5 | 6 | 7 | 8 | 24 |
|---|---|---|---|---|---|---|---|---|---|---|
| 1 | 17,46 | 26,33 | 40,62 | 52,29 | 58,81 | 64,87 | 70,26 | 77,36 | 80,49 | 95,53 |
| 2 | 26,42 | 42,72 | 63,05 | 76,74 | 86,06 | 92,15 | 94,73 | — | — | 98,77 |
| 3 | 22,08 | 34,96 | 55,66 | 68,94 | 76,69 | 84,19 | 88,62 | 91,76 | 92,68 | 98,38 |
| 4 | 17,91 | 27,60 | 42,26 | 54,37 | 61,41 | 71,36 | 75,82 | 81,39 | 86,52 | 99,99 |
| 5 | 28,06 | 47,08 | 69,44 | 83,82 | 89,88 | 95,61 | 95,88 | — | — | 97,31 |
| 6 | — | 24,61 | 41,05 | 56,80 | 61,77 | 69,43 | 75,43 | — | 85,31 | — |
| 7 | — | 14,70 | 27,21 | 41,34 | 48,88 | 58,72 | 67,40 | — | 77,73 | — |
| 8 | — | 1,11 | 1,64 | 5,49 | 8,82 | 13,14 | 16,89 | — | 24,08 | — |
| 9 | — | — | — | 5,50 | 9,78 | 13,71 | 29,03 | — | 42,62 | — |

What we claim is:

1. Binder-free granules for oral and parenteral administration with delayed release of the active compound consisting of a pharmaceutical active compound or granules thereof and poly-D(—)-3-hydroxybutyric acid having a molecular weight of about 50,000 to about 800,000, wherein the active compound or granules thereof is/are coated with an amount of 1 to 20% by weight of said poly-D(—)-3-hydroxybutyric acid, based on the total weight.

2. Binder-free granules as claimed in claim 1, wherein the active compound or granules thereof is/are coated with an amount of 1 to 15% of poly-D(—)-3-hydroxybutyric acid, based on the total weight.

3. Binder-free granules as claimed in claim 1, wherein the active compound or granules thereof is/are coated with an amount of 3 to 10% of poly-D(—)-3-hydroxybutyric acid, based on the total weight.

4. Binder-free granules as claimed in claim 1, wherein the active compound is 7-hydroxyethyltheophylline.

5. Binder-free granules as claimed in claim 1, wherein the molecular weight of the poly-D(—)-3-hydroxybutyric acid used is between 100,000 and 400,000.

6. Binder-free granules as claimed in claim 1, wherein the active compound is celiprolol hydrochloride.

7. Binder-free granules as claimed in claim 1, which have been prepared by fluidized bed granulation.

8. Binder-free granules as claimed in claim 1, wherein the active compound is hexobendine dichloride.

9. Binder-free granules as claimed in claim 1, wherein the active compound is ibuprofen.

10. Binder-free granules as claimed in claim 1, wherein the active compound is dichlofenac-Na.

* * * * *